(12) United States Patent
Sutton et al.

(10) Patent No.: US 11,318,286 B2
(45) Date of Patent: May 3, 2022

(54) CATHETER NEEDLE ASSEMBLY WITH ENCLOSABLE NEEDLE

(71) Applicant: I-V Access Technology, Inc., San Francisco, CA (US)

(72) Inventors: Thomas Sutton, Summit, NJ (US); Jacob Hentzler, Morgan Hill, CA (US); James Hale, Los Osos, CA (US); Vincent Leskowich, Oakhust, NH (US)

(73) Assignee: I-V Access Technology, Inc., San Francisco, CA (US)

( * ) Notice: Subject to any disclaimer, the term of this patent is extended or adjusted under 35 U.S.C. 154(b) by 0 days.

(21) Appl. No.: 17/208,962

(22) Filed: Mar. 22, 2021

(65) Prior Publication Data

US 2021/0290911 A1 Sep. 23, 2021

Related U.S. Application Data

(60) Provisional application No. 62/993,493, filed on Mar. 23, 2020, provisional application No. 63/037,841, filed on Jun. 11, 2020.

(51) Int. Cl.
*A61M 25/06* (2006.01)
*A61M 25/00* (2006.01)

(52) U.S. Cl.
CPC .... *A61M 25/0612* (2013.01); *A61M 25/0097* (2013.01); *A61M 25/0606* (2013.01); *A61M 25/0693* (2013.01)

(58) Field of Classification Search
CPC .......... A61M 25/0612; A61M 25/0097; A61M 25/0606; A61M 25/0625; A61M 25/0693
See application file for complete search history.

(56) References Cited

U.S. PATENT DOCUMENTS

| | | | |
|---|---|---|---|
| 3,195,786 A | 7/1965 | Vogt | |
| 3,347,232 A | 10/1967 | Abraham | |
| 3,861,416 A | 1/1975 | Wichterle | |
| 4,341,239 A | 7/1982 | Atkinson | |
| 4,465,102 A | 8/1984 | Rupp | |
| 4,524,805 A | 6/1985 | Hoffman | |
| 4,565,545 A | 1/1986 | Suzuki | |
| 4,588,398 A | 5/1986 | Daugherty et al. | |
| 4,629,450 A | 12/1986 | Suzuki et al. | |
| 4,655,752 A | 5/1987 | Honkanen et al. | |
| 4,758,225 A | 7/1988 | Cox et al. | |
| 4,950,257 A | 8/1990 | Hibbs et al. | |
| 5,010,925 A | 4/1991 | Atkinson et al. | |
| 5,092,857 A | 3/1992 | Fleischhacker | |
| 5,114,407 A | 5/1992 | Burbank | |
| 5,114,408 A | 5/1992 | Fleischhaker et al. | |
| 5,122,118 A | 6/1992 | Haber et al. | |

(Continued)

FOREIGN PATENT DOCUMENTS

| | | |
|---|---|---|
| CN | 203694357 | 7/2014 |
| EP | 0653220 | 5/1995 |

(Continued)

*Primary Examiner* — Theodore J Stigell

(74) *Attorney, Agent, or Firm* — Levine Bagade Han LLP

(57) ABSTRACT

Methods and devices to facilitate positioning of a catheter into a vessel. Devices include axially concentric assemblies of a piercing cannula, a shield and tubing such as a catheter where the shield can be passively or actively locked into position over the cannula tip to prevent inadvertent needle sticks.

22 Claims, 13 Drawing Sheets

(56) References Cited

U.S. PATENT DOCUMENTS

| | | |
|---|---|---|
| 5,129,884 A | 7/1992 | Dysarz |
| 5,176,650 A | 1/1993 | Haining |
| 5,242,410 A | 9/1993 | Melker |
| 5,295,658 A | 3/1994 | Atkinson et al. |
| 5,405,323 A | 4/1995 | Rogers et al. |
| 5,445,617 A | 8/1995 | Yoon |
| 5,456,284 A | 10/1995 | Ryan et al. |
| 5,527,290 A | 6/1996 | Zadini et al. |
| 5,618,272 A | 4/1997 | Nomura |
| 5,713,876 A | 2/1998 | Bogert et al. |
| 5,843,046 A | 12/1998 | Motisi et al. |
| 6,035,896 A | 3/2000 | Liardet |
| 6,165,168 A | 12/2000 | Russo |
| 6,267,748 B1 | 7/2001 | Gulliksen et al. |
| 6,607,511 B2 | 8/2003 | Halseth et al. |
| 6,702,255 B2 | 3/2004 | Dehdashtian |
| 6,706,017 B1 | 3/2004 | Dulguerov |
| 6,716,197 B2 | 4/2004 | Svendsen |
| 6,817,989 B2 | 11/2004 | Svendsen et al. |
| 7,001,396 B2 | 2/2006 | Glazier et al. |
| 7,470,254 B2 | 12/2008 | Basta et al. |
| 7,736,339 B2 | 6/2010 | Woehr et al. |
| 7,753,338 B2 | 7/2010 | Desecki |
| 7,892,209 B2 | 2/2011 | Harand et al. |
| 7,938,805 B2 | 5/2011 | Harding et al. |
| 8,006,953 B2 | 8/2011 | Bennett |
| 8,021,338 B2 | 9/2011 | Adams |
| 8,092,432 B2 | 1/2012 | Nordgren |
| 8,105,288 B2 | 1/2012 | Keyser et al. |
| 8,469,928 B2 | 6/2013 | Stout et al. |
| 8,591,469 B2 | 11/2013 | Keyser et al. |
| 8,900,192 B2 | 12/2014 | Anderson et al. |
| 8,915,884 B2 | 12/2014 | Tai et al. |
| 9,028,425 B2 | 5/2015 | Burkholz |
| 9,114,231 B2 | 8/2015 | Woehr et al. |
| 9,155,863 B2 | 10/2015 | Isaacson et al. |
| 9,155,864 B2 | 10/2015 | Stout et al. |
| 9,604,035 B2 | 3/2017 | Keyser et al. |
| 9,764,117 B2 | 9/2017 | Bierman et al. |
| 9,775,973 B2 | 10/2017 | Keyser et al. |
| 9,851,268 B2 | 12/2017 | Eichhorn et al. |
| 10,004,533 B2 | 6/2018 | Entabi |
| 10,010,343 B2 | 7/2018 | Bierman et al. |
| 10,136,916 B2 | 11/2018 | Bierman et al. |
| 10,406,326 B2 | 9/2019 | Solomon |
| 10,441,752 B2 | 10/2019 | Bierman et al. |
| 10,569,059 B2 | 2/2020 | Bierman |
| 10,682,157 B2 | 6/2020 | Bierman et al. |
| 10,850,069 B2 | 12/2020 | Solomon |
| 2004/0092879 A1 | 5/2004 | Kraus et al. |
| 2004/0097880 A1 | 5/2004 | Schur |
| 2004/0193109 A1 | 9/2004 | Prestidge et al. |
| 2004/0236287 A1* | 11/2004 | Swenson ............ A61M 5/3245 604/263 |
| 2005/0131350 A1 | 6/2005 | Shaw et al. |
| 2005/0187524 A1 | 8/2005 | Willis et al. |
| 2005/0256460 A1 | 11/2005 | Rome et al. |
| 2006/0200083 A1 | 9/2006 | Freyman et al. |
| 2007/0250037 A1 | 10/2007 | Brimhall et al. |
| 2007/0282268 A1 | 12/2007 | Mayse |
| 2008/0092571 A1 | 4/2008 | Allison et al. |
| 2008/0093571 A1 | 4/2008 | Desecki |
| 2008/0172003 A1 | 7/2008 | Plishka et al. |
| 2009/0209912 A1 | 8/2009 | Keyser et al. |
| 2009/0209914 A1 | 8/2009 | Koch et al. |
| 2011/0056569 A1 | 3/2011 | Chambo et al. |
| 2012/0150118 A1 | 6/2012 | Keyser et al. |
| 2012/0221024 A1 | 8/2012 | Sutton et al. |
| 2013/0204226 A1 | 8/2013 | Keyser |
| 2014/0058357 A1 | 2/2014 | Keyser et al. |
| 2014/0275795 A1 | 9/2014 | Little et al. |
| 2014/0276432 A1* | 9/2014 | Bierman ............ A61B 17/3498 604/164.1 |
| 2015/0265827 A1 | 9/2015 | Keyser et al. |
| 2016/0228654 A1 | 8/2016 | Rozwadowski et al. |
| 2016/0271370 A1 | 9/2016 | Keyser et al. |
| 2017/0326341 A1 | 11/2017 | Liska |
| 2018/0064912 A1 | 3/2018 | Keyser et al. |
| 2019/0060616 A1 | 2/2019 | Solomon |
| 2020/0016375 A1 | 1/2020 | Solomon |
| 2020/0061346 A1 | 2/2020 | Solomon |
| 2021/0031009 A1 | 2/2021 | Solomon |
| 2021/0268238 A1 | 9/2021 | Solomon et al. |

FOREIGN PATENT DOCUMENTS

| | | |
|---|---|---|
| EP | 1291035 | 3/2003 |
| EP | 2269685 | 1/2011 |
| FR | 2655859 | 6/1991 |
| FR | 2687320 | 8/1993 |
| JP | 07-136285 | 5/1995 |
| JP | 09-047512 | 2/1997 |
| JP | 2007-260218 | 10/2007 |
| JP | 2011-234802 | 11/2011 |
| TW | 368422 | 9/1999 |
| TW | 592741 | 6/2004 |
| WO | WO 1992/016248 | 10/1992 |
| WO | WO 2003/013627 | 2/2003 |
| WO | WO 2009/091514 | 7/2009 |
| WO | WO 2013/119557 | 8/2013 |
| WO | WO 2015/142850 | 9/2015 |
| WO | WO 2018/132758 | 7/2018 |
| WO | WO 2019/046456 | 3/2019 |
| WO | WO 2020/191228 | 9/2020 |
| WO | WO 2021/194979 | 9/2021 |

* cited by examiner

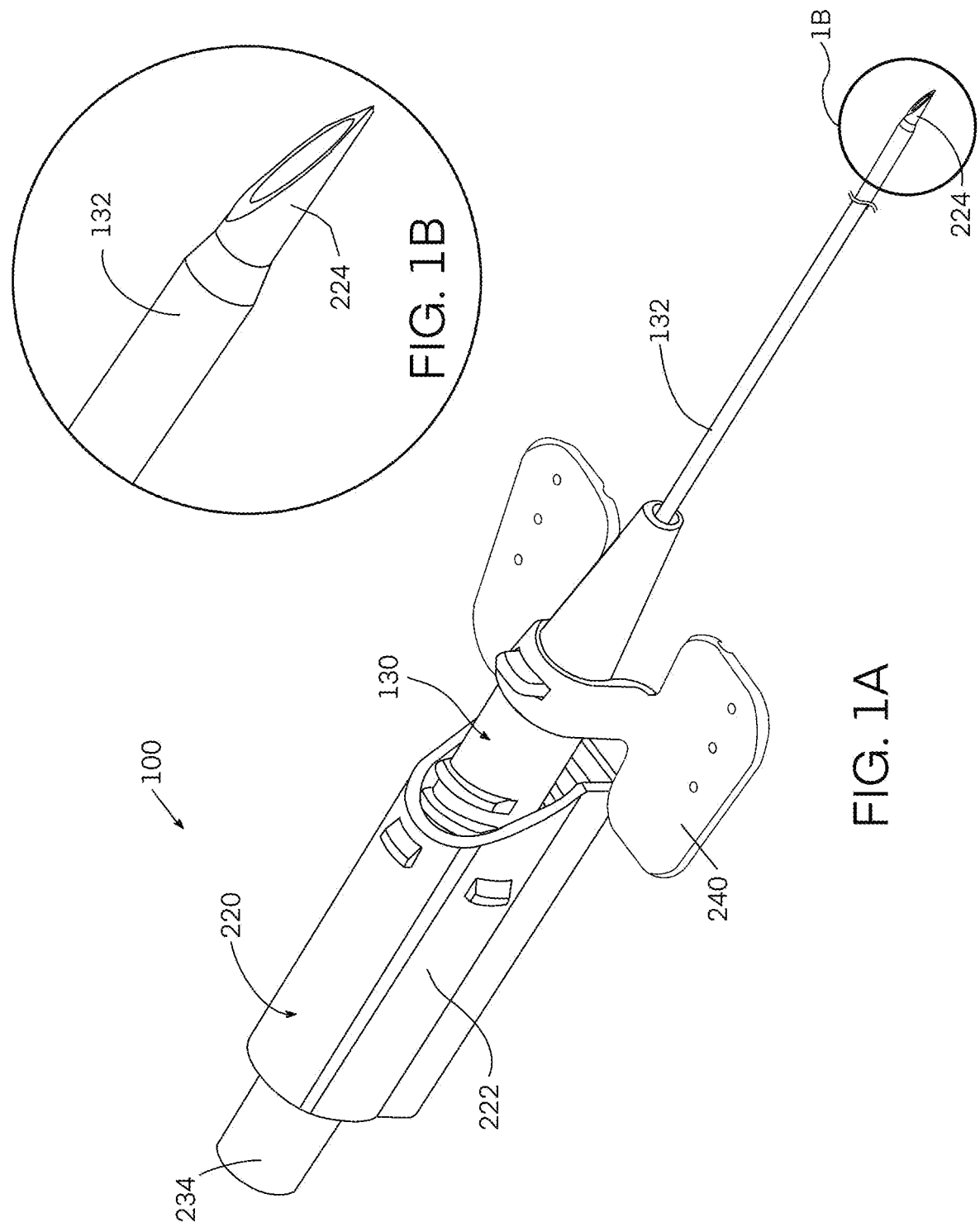

Conventional Needle and Catheter size comparison based on ISO 10555-5-Table 1 and ISO 9626 Needle size for needles 2 gauge sizes smaller (Standard/General Catheter Sizing)

| Configuration | Needle Size | Nominal Needle OD | Catheter Size | Nominal Catheter OD | Percent increase from needle to catheter OD | Percent decrease from catheter to needle OD | Needle OD percentage of catheter OD |
|---|---|---|---|---|---|---|---|
| 14G | 16G | 0.065 | 14G | 0.079 | 22 | 18 | 82 |
| 16G | 18G | 0.049 | 16G | 0.067 | 37 | 27 | 73 |
| 18G | 20G | 0.035 | 18G | 0.049 | 40 | 29 | 71 |
| 20G | 22G | 0.028 | 20G | 0.041 | 46 | 32 | 68 |
| 22G | 24G | 0.022 | 22G | 0.033 | 50 | 33 | 67 |
| 24G | 26G | 0.018 | 24G | 0.028 | 56 | 36 | 64 |

Examples of Various 3rd Party Needle and Catheter Assemblies for reference (All older, non-valved product)

| Device | Needle Size | Nominal Needle OD | Catheter Size | Nominal Catheter OD | Percent increase from needle to catheter OD | Percent decrease from catheter to needle OD | Needle OD percentage of catheter OD |
|---|---|---|---|---|---|---|---|
| 18G B.Braun Introcan | 20G | 0.036 | 18G | 0.053 | 47 | 32 | 68 |
| 18G Smiths Protect IV | 20G | 0.036 | 18G | 0.052 | 44 | 31 | 69 |
| 18G BD Insyte Autoguard | 20G | 0.035 | 18G | 0.052 | 49 | 33 | 67 |
| 20G B.Braun Introcan | 22G | 0.028 | 20G | 0.045 | 61 | 38 | 62 |
| 20G Smiths Protect IV | 22G | 0.028 | 20G | 0.044 | 57 | 36 | 64 |
| 20G BD Insyte Autoguard | 22G | 0.028 | 20G | 0.042 | 50 | 33 | 67 |
| 22G B.Braun Introcan | 24G | 0.022 | 22G | 0.034 | 55 | 35 | 65 |
| 22G Smiths Protect IV | 24G | 0.022 | 22G | 0.036 | 64 | 39 | 61 |
| 22G BD Insyte Autoguard | 24G | 0.023 | 22G | 0.035 | 52 | 34 | 66 |
| 24G B.Braun Introcan | 27G | 0.016 | 24G | 0.027 | 69 | 41 | 59 |
| 24G Smiths Protect IV | 26G | 0.018 | 24G | 0.029 | 61 | 38 | 62 |
| 24G BD Insyte Autoguard | 26G | 0.018 | 24G | 0.028 | 56 | 36 | 64 | all OD values in inches

FIG. 11A

W Access Technology Design

| Configuration | Needle Size | Nominal Needle OD | Catheter Size | Nominal Catheter OD | Percent increase from needle to catheter OD | Percent decrease from catheter to needle OD | Needle OD percentage of catheter OD |
|---|---|---|---|---|---|---|---|
| 14G | 18G | 0.05 | 14G | 0.078 | 56 | 36 | 64 |
| 16G | 20G | 0.036 | 16G | 0.064 | 78 | 44 | 56 |
| 18G | 22G | 0.028 | 18G | 0.051 | 82 | 45 | 55 |
| 20G | 24G | 0.022 | 20G | 0.043 | 95 | 49 | 51 |
| 22G | 26G | 0.018 | 22G | 0.036 | 100 | 50 | 50 |
| 24G | 28G | 0.014 | 24G | 0.028 | 100 | 50 | 50 | all OD values in inches

FIG. 11B

CATHETER NEEDLE ASSEMBLY WITH ENCLOSABLE NEEDLE

CROSS-REFERENCE TO RELATED APPLICATIONS

This application claims the benefit of U.S. Provisional Applications 62/993,493 filed on Mar. 23, 2020 and 63/037,841 filed on Jun. 11, 2020, the entirety of both of which are incorporated herein by reference.

FIELD OF THE INVENTION

Methods and devices to facilitate positioning of a catheter into a vessel. Devices include axially concentric assemblies of a piercing needle, a shield and catheter where the shield can be passively or actively locked into position over the needle tip to prevent inadvertent needle sticks.

BACKGROUND

Intravenous venous catheterization involves the insertion of a small catheter into a peripheral blood vessel, typically for the administration of medication, fluids or drawing of blood. The act of inserting an intravenous catheter presents risks to both healthcare workers and patients. For example, healthcare workers face a risk of infection upon being exposed to a patient's bodily fluids. In addition, when the healthcare worker removes a needle used during catheterization of the patient, the healthcare worker must take significant care to prevent the sharp needle from inadvertently penetrating the skin of the healthcare worker.

Another concern involves the patient. Namely, to successfully access veins, even small, fragile or traumatically stressed ones, there is a desire to minimize the trauma and minimize the size of the introducer needle. This concern is balanced against the need for the needle to allow for introduction of a catheter over the needle and into the vessel.

Once the catheter is properly inserted, it is important to minimize fluid or blood leakage from the proximal end of the catheter while a connector is coupled to the inserted catheter. It is also important to protect caregivers and other individuals from used needles.

The devices, methods and systems described herein provide for an improved catheter and/or needle assembly.

SUMMARY

The illustrations and variations described herein are meant to provide examples of the methods and devices of the invention. It is contemplated that combinations of aspects of specific embodiments or combinations of the specific embodiments themselves are within the scope of this disclosure. The devices and methods described herein are discussed as an exemplary embodiment of a catheter needle assembly. However, with catheters or other medical devices/introducers including but not limited to catheters, introducers, tubes, lines, ports that can be used for vascular or other devices.

The present disclosure includes medical assemblies for insertion into tissue. In one example, a variation of a medical assembly includes a cannula assembly comprising a cannula hub and a cannula member extending to a cannula distal end; a shield assembly comprising a shield hub and a shield member extending to a shield distal end, where the shield hub is configured to be received in the cannula hub and the shield member is configured to concentrically receive the cannula member, where the shield assembly is configured to move from a ready configuration to a safe configuration; a tubing assembly comprising a tubing hub and a tubing extending to a tubing distal end, where the tubing assembly is configured to be received in the cannula hub over the shield hub and where the tubing is configured to concentrically receive the shield member; wherein in the ready configuration the shield hub is releasably locked to the tubing hub, the cannula distal end extends beyond both the shield distal end and the tubing distal end to permit insertion into tissue, and the shield distal end remains within the tubing; where, when in the ready configuration, relative movement between the tubing hub and the cannula hub by a first distance causes movement of the shield assembly to the safe configuration; and wherein in the safe configuration, the shield hub is released from the tubing hub and mechanically interferes with the cannula hub to become locked thereto, and the shield distal end now extends distally to the cannula distal end while remaining within the tubing.

The relative movement described herein can include advancing the tubing hub distally while the cannula hub remains stationary or is moved proximally. In some variations where the assembly is positioned in a small vessel, the tubing hub can remain stationary while the cannula hub is withdrawn proximally.

Variations of the medical assembly described herein can include a blunted distal end of the cannula or a sharp tip.

The medical assemblies described herein can include a locking arm that is spring biased away from the shield hub and the cannula hub comprises a first guide surface within an interior of the cannula hub, wherein in the ready configuration the locking arm is urged against the tubing hub by the first guide surface to releasably lock the shield hub to the tubing hub.

In additional variations, the interior of the cannula hub can further include a first locking surface spaced from the first guide surface and wherein in the safe configuration, the locking arm disengages from the first guide surface causing the locking arm to bias away from the tubing hub towards the cannula hub such that a second locking surface of the locking arm mechanically interferes with the first locking surface to prevent distal movement of the shield hub out of to the cannula hub. Any number of locking and guiding surfaces are within the scope of the disclosure.

Variations of the medical assembly include a safe configuration where the locking arm entirely disengages from the first guide surface. Furthermore, in the safe configuration the locking arm can mechanically interfere with the first guide surface to prevent proximal movement of the shield hub within the cannula hub.

Variations of the devices described herein also include a shield member that reinforces the tubing to permit the tubing to have a gauge difference of at least 3 sizes between the tubing and the cannula. Moreover, the tubing distal end can comprise a plurality of openings to allow for increased flow through a distal end in view of the greater size differential between the lumen diameter and the diameter of a distal opening of the tubing.

In variations of the devices, the tubing can comprise a catheter tubing and the cannula can comprise a needle.

In additional variations, the shield distal end can comprise a blunted distal end. However, variations include a shield distal end that presents less of a risk of accidental penetration into tissue as compared to the cannula distal end.

Variations of the devices can include a portion of the cannula hub that comprises a flash chamber configured to visually confirm fluids in the cannula hub.

An additional variation of a medical assembly for insertion into tissue includes: a cannula assembly having a cannula hub and a cannula having a cannula distal end, the cannula hub having an interior chamber with a first guide surface and a first locking surface; a shield assembly comprising a shield hub and a shield member having a shield distal end, the shield hub configured to be received within the interior chamber of the cannula hub such that the cannula is coaxially received in the shield member, the shield hub comprising a locking arm having a second locking surface and a second guide surface, the locking arm also having an intermediate portion extending between a fixed portion and a free portion, where the fixed portion is coupled to the shield hub and the free portion is spring-biased away from the shield hub, the shield assembly being moveable between a ready configuration and a safe configuration; a tubing assembly comprising a tubing hub and a tubing member having a tubing distal end, wherein the tubing hub is configured for positioning on the shield hub and the tubing member coaxially receives the shield member, the tubing hub comprising a surface feature; wherein in the ready configuration the cannula distal end extends distally beyond both the shield distal end and the tubing distal end and where the first guide surface engages the second guide surface to constrain the free portion of the locking arm against the surface feature of the tubing hub to releasably lock the shield hub to the tubing hub; wherein, when in the ready configuration, axial separation of the tubing hub from the cannula hub over a first distance causes the shield assembly to assume the safe configuration where the second guide surface disengages from the first guide surface causing the free portion to bias away from and disengage the tubing hub, and where the shield distal end is now positioned distal to the cannula distal end, and where interference between the second locking surface against the first locking surface prevents further axial separation of the shield hub from the cannula hub to permit separation of the tubing assembly from the shield assembly and the cannula assembly.

The present disclosure also includes a method of inserting a medical assembly into tissue and removing the medical assembly from tissue in a safe condition, the method comprising: positioning the medical assembly adjacent to tissue where a cannula end of a cannula extends distally from a tubing end of a tubing and where a shield member is located between the cannula and the tubing, the shield member having a shield end that is located within the tubing, and where medical assembly includes a cannula hub joined to the cannula, a tubing hub joined to the tubing, and a shield hub joined to the shield member, where the tubing hub is seated on the shield hub and releasably locked thereto, and the shield hub is seated on the cannula hub; inserting the cannula end and the tubing end into tissue to a desired location; moving the tubing hub relative to the cannula hub such that the shield hub moves with the tubing hub causing the shield end to be positioned distally to the tubing end while remaining within the tubing, and causing the shield hub to release from the tubing hub while mechanically locking with the cannula hub; and removing the shield member and the cannula from the tubing and the tubing hub such that the shield member covers the cannula to establish the safe condition.

The method can further include visually identifying a fluid within the cannula hub prior to removing the shield member and the cannula from the tubing.

In an additional variation, the medical assemblies described herein can include a cannula extending from a cannula hub to a cannula distal end; a shield member extending from a shield hub to a shield distal end, the shield member positioned over the cannula, where shield distal end member is located proximally to the cannula end; a tubing extending from a tubing hub to a tubing distal end, the tubing positioned over the shield member, where the tubing distal end extends distally to the shield distal end such that tubing distal end tapers to contact the cannula at a location distally to the shield member; wherein the cannula includes a protected position when the cannula is moved proximally relative to both the shield member and tubing such that the cannula distal end is located within the shield member; and wherein the shield member and the cannula are removable from the catheter tubing.

An additional variation of the devices can include a needle assembly having a cannula extending from a cannula hub to a cannula distal end, the cannula comprising a first gauge size; a shield member extending from a shield hub slidably to a shield distal end, the shield member positioned over the cannula, where the shield distal end is located proximally to the cannula distal end; a tubing having a second gauge size and extending from a tubing hub to a tubing distal end, the tubing positioned over the shield member, where the tubing distal end extends distally to the shield distal end such that the tubing distal end tapers to contact the cannula at a location distal to the shield distal end; and wherein the first gauge size is smaller than the second gauge size by at least a three gauge differential.

The methods, devices, and systems described herein provides several benefits over conventional needle systems. For example, the needle assemblies described herein allow for insertion of the catheter using a small gauge needle that is undersized relative to a larger size catheter as compared to conventional catheter needle assemblies. The catheter assemblies of the current disclosure incorporate a dilator or similar support member between the catheter tubing and needle cannula as a support rather than to dilate tissue. Such a configuration allows passage of the assembly into the vessel allowing for an easy introduction of the catheter into the vein or other body target. The use of a smaller needle and dilator can reduce pain and/or anxiety of the patient as well as reduce the risk of vascular damage. In addition, the devices described herein can allow for active or passive covering of the sharp cannula tip through movement of the tubing assembly.

In addition, the catheters described herein can employ a one way, blood control valve that reduces the risk of blood leakage, until catheter is fluidly coupled to a separate line.

The present disclosure is related to the following commonly assigned patents and applications, the entirety of each of which is incorporated by reference: U.S. Pat. No. 8,105,288 issued on Jan. 31, 2012, U.S. Pat. No. 8,591,469 issued on Nov. 26, 2013, U.S. Pat. No. 9,775,973 issued on Oct. 3, 2017, U.S. Pat. No. 9,604,035 issued on Mar. 28, 2017, U.S. Pat. No. 10,828,465 issued on Nov. 10, 2020, U.S. Pat. No. 10,052,474 issued on Aug. 21, 2018, U.S. Pat. No. 10,406,326 issued on Sep. 10, 2019, U.S. Pat. No. 10,850,069 issued on Dec. 1, 2020, U.S. Patent Publication no.: US20190038889 published on Feb. 7, 2019, U.S. Patent Publication no.: US20190351210 published on Nov. 21, 2019, U.S. Patent Publication no.: US20200016375 published on Jan. 16, 2020, U.S. Patent Publication no.: US20210031009 published on Feb. 4, 2021, and PCT publication WO2020191228 published on Sep. 24, 2020.

BRIEF DESCRIPTION OF THE DRAWINGS

Each of the following figures diagrammatically illustrates aspects and variations to better understand the invention. Variation of the invention from the aspects shown in the figures is contemplated.

FIG. 1A illustrates an example of an improved needle-catheter assembly with a removable wing used for securing the catheter to a surface of tissue when the catheter is positioned within a vessel.

FIG. 1B shows a magnified view of a distal end of the section 1B of the needle-catheter assembly in FIG. 1A.

FIG. 11A shows a table conventional needle and catheter sizes.

FIG. 11B shows a table of configurations of catheter needle assemblies constructed in accordance with the present disclosure.

DETAILED DESCRIPTION

Figure 2A:
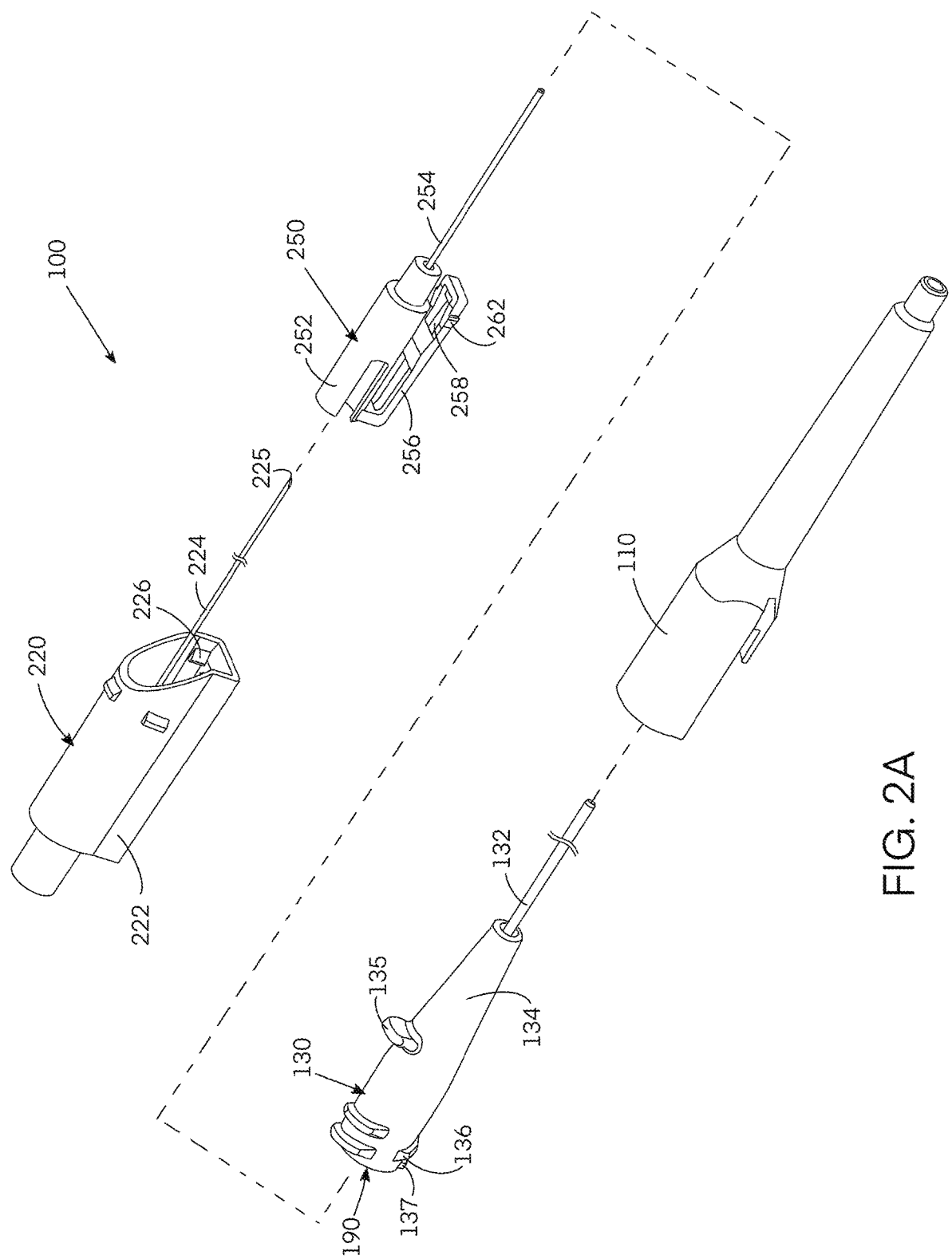
FIG. 2A illustrates an exploded view of a variation of a catheter needle assembly 100 having a needle assembly, a support/shield assembly, a catheter and a safety cap.

For a better understanding of the present invention, reference will be made to the following Description of the Embodiments, which is to be read in association with the accompanying drawings, which are incorporated in and constitute a part of this specification, show certain aspects of the subject matter disclosed herein and, together with the description, help explain some of the principles associated with the disclosed implementations.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising. (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

FIG. 1A illustrates an example of an improved needle-catheter assembly 100 with a removable wing 240 used for securing the catheter 130 to a surface of tissue when the catheter is positioned within a vessel. The needle-catheter assembly 100 shown in FIG. 1A includes a needle assembly 220 having a needle hub 222 coupled to the catheter 130 through an intermediate support/shield hub (not shown in FIG. 1A). The catheter 130 includes a catheter tubing/extrusion 132 terminating proximally to an end of a needle cannula 172 as shown in FIG. 1B, which is a magnified view of area 1B from FIG. 1A. Any portion of the needle assembly 220 and components positioned therein (such as the support/shield hub and/or catheter hub) can include transparent or translucent sections to allow for visual detection of blood or fluid flow therein. In one example a proximal portion 234 if a needle hub 222 can comprise a visually transparent/translucent flashback chamber.

As shown in FIG. 1B, variations of the device include a distal end of the catheter tubing 132 directly contacting the needle cannula 224 at a distal end of the assembly. As discussed below, the use of an intermediate member (not shown in FIG. 1A or 1B) as a support structure allows for an increased step in diameter or gauge size between the needle cannula 224 and catheter tubing 132. Traditional devices typically employ a dilator allow for a size difference between a needle and catheter when inserting an assembly into a blood vessel. However, variations of the assemblies 100 described herein can Such a step can include a 3- or 4-gauge size difference between the size (outer diameter) of the catheter and the size of the needle. Alternate variations allow for a conventional 2-gauge size between the needle cannula 224 and catheter tubing 132. The support/shield member can serve a second purpose as a shielding element that covers the distal tip of the needle cannula to render the used needle assembly in a safe non-stick configuration. Accordingly, the intermediate member can function as a support/shield assembly. Variations of the present disclosure can also include conventional needle assembly tip designs where the distal end of the catheter tubing terminates on a support/shield cannula or tubing, which then terminates on a needle cannula.

FIG. 2A illustrates an exploded view of a variation of a catheter needle assembly 100 having a needle assembly 220, a support/shield assembly 250, a catheter 130 and a safety cap 110. Variations of the devices and methods under the present invention can include needle assemblies that do not include a cap 110.

In the variation shown by FIG. 2A, the needle-catheter assembly 100 includes a needle assembly 220 that seats a support/shield assembly 250. The shield assembly then couples to a catheter 130. As discussed below, the needle-catheter assembly 100 can include a ready configuration where the support/shield assembly 250 is initially releasably joined to the catheter 130 such that the needle tip 225 is exposed. This configuration permits a caregiver to insert the needle-catheter assembly 100 into tissue of a patient and ultimately into a blood vessel. Actuation of the needle-catheter assembly 100 by the caregiver causes the support/shield assembly 250 to release from the catheter 130 while becoming locked to the needle assembly 220. In this locked configuration, the sharp tip 225 of the needle cannula 224 moves within the support/shield tubing 254, which then functions as a shield. In such variations, the support/shield tubing 254 can also be described as a shield tubing or shield element. In some variations of the assembly 100, the distal end of the support/shield tubing 254 is rounded or blunt to further protect the caregiver. Alternatively, the distal end of the support/shield 254 tubing can have a taper to match to an internal taper of the catheter tip.

FIG. 2A further illustrates the support/shield assembly 250 including a support/shield hub 252 having a locking arm 256. The locking arm can include any number of features to facilitate the configurations described above. The locking arm 256 can have a biased configuration such that it biases away a hub 252 of the support/shield assembly 250. As shown, the locking arm 256 is parallel or near parallel to the support/shield hub 252, which is the position of the locking arm 256 when nested within the needle hub 222. The variation of the support/shield assembly 250 shown in FIG. 2A includes a locking arm having a slot or opening 258 and provides any number of locking features and/or mating features to facilitate the locking positions discussed herein. Locking features 262 can lock against locking feature 226 of the needle hub 222 to lock the support/shield assembly 250 to the needle assembly 220.

As described above, the assembly illustrated in FIG. 2A (or any assembly disclosed herein) includes a catheter 130. However, variations of the invention can include embodiments without a catheter.

FIG. 2A also illustrates the catheter 130 including a catheter hub 134 having a catheter tubing 132 extending from the hub 134. The catheter hub 134 includes proximal threading 136 as well as any number of surfaces 135 that can be used by a caregiver to manipulate or handle the catheter 130. The internal opening of the catheter hub 134 at a proximal end (e.g., adjacent to the threading 136) can include a standard luer taper to accommodate male luer fittings as well as any type of valve 190 to prevent leakage of blood from the catheter 130. As discussed below, the threading 136 of the catheter hub 134 can also serve as a surface feature or locking surfaces during deployment and positioning of the catheter tube 132 in a vessel. In alternate variations, the catheter can include any number of surface features 137, other than threading, where such features function as locking surfaces.

Figure 2B:
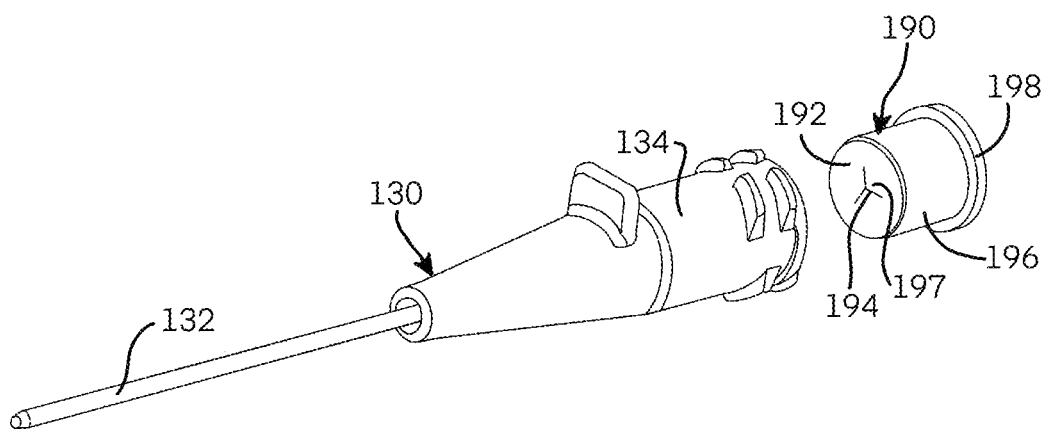
FIGS. 2B to 2D illustrate an improved valve for use with catheter.
Figure 2C:
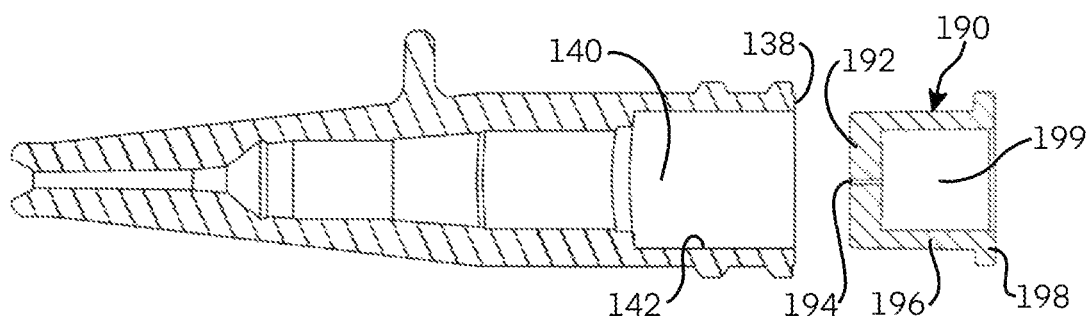
Figure 2D:
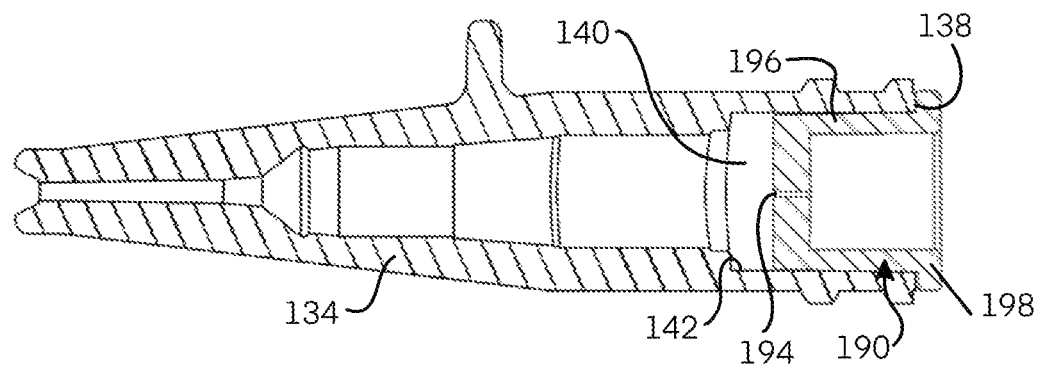

FIGS. 2B-2D illustrate an improved valve for use with catheters, including a catheter as described herein. Typically, such a catheter 130 is used with a male luer that is inserted into the catheter body 134 through the valve 190. The catheter 130 includes a catheter hub 134 having a chamber 140 with a proximal surface 138 defining an open proximal end. The chamber 140 is in fluid communication with a catheter tubing 132 that is coupled to the catheter. The tubing includes one or more lumens in fluid communication with the chamber 140. The valve or septum valve 190 includes a barrier layer (or septum) 192 at a distal end. The barrier layer 192 can have one or more slits 194. The illustrated variation shows a barrier layer 192 with 3 slits 194 that form three leaflet structures 197 or flaps. However, variations of the valve 190 include any number of slits forming any number of leaflets. The barrier layer 192 generally includes a flexible or semi-flexible material that is compatible with exposure to blood, medicaments, and other fluids commonly encountered during catheterization/infusion procedure.

As shown in FIG. 2C, the valve includes a wall portion 196 extending proximally from the barrier layer 192 and defines a valve cavity 199. A flange portion 198 is formed around the wall 196 at a proximal end of the valve 190. The flange portion comprises a diameter greater than a diameter of the wall portion. Variations of the valve 190 include a flange portion 198 that encircles the valve 190. Alternatively, the flange portion 198 can include openings or segments such that it is not circumferentially continuous about the wall.

FIG. 2D shows the valve 190 coupled to the catheter hub 134 such that the flange portion 198 engages the proximal surface 138 of the catheter hub 134 and is exterior to the chamber 140 of the hub 134. The wall portion 196 of the valve 190 engages a surface of the chamber. The valve 190 can be affixed to the catheter at various points. For example, variations of the assembly include a valve 190 that is only affixed to the catheter hub 134 at the flange portion 198 using an adhesive or joining material where the wall portion 196 is simply positioned against a wall of the chamber 140. Alternatively, or in combination, the valve 190 can be affixed to the catheter hub 134 at the exterior wall portion 196. In an alternate variation, the valve 190 can simply be press-fit into the catheter hub 134. Any number of features known to those in the art can be used to facilitate seating of the valve 190 within the catheter hub 134 (e.g., pockets, ribs, increased frictional resistance of the surface of the valve or chamber, etc.)

Figure 3A:
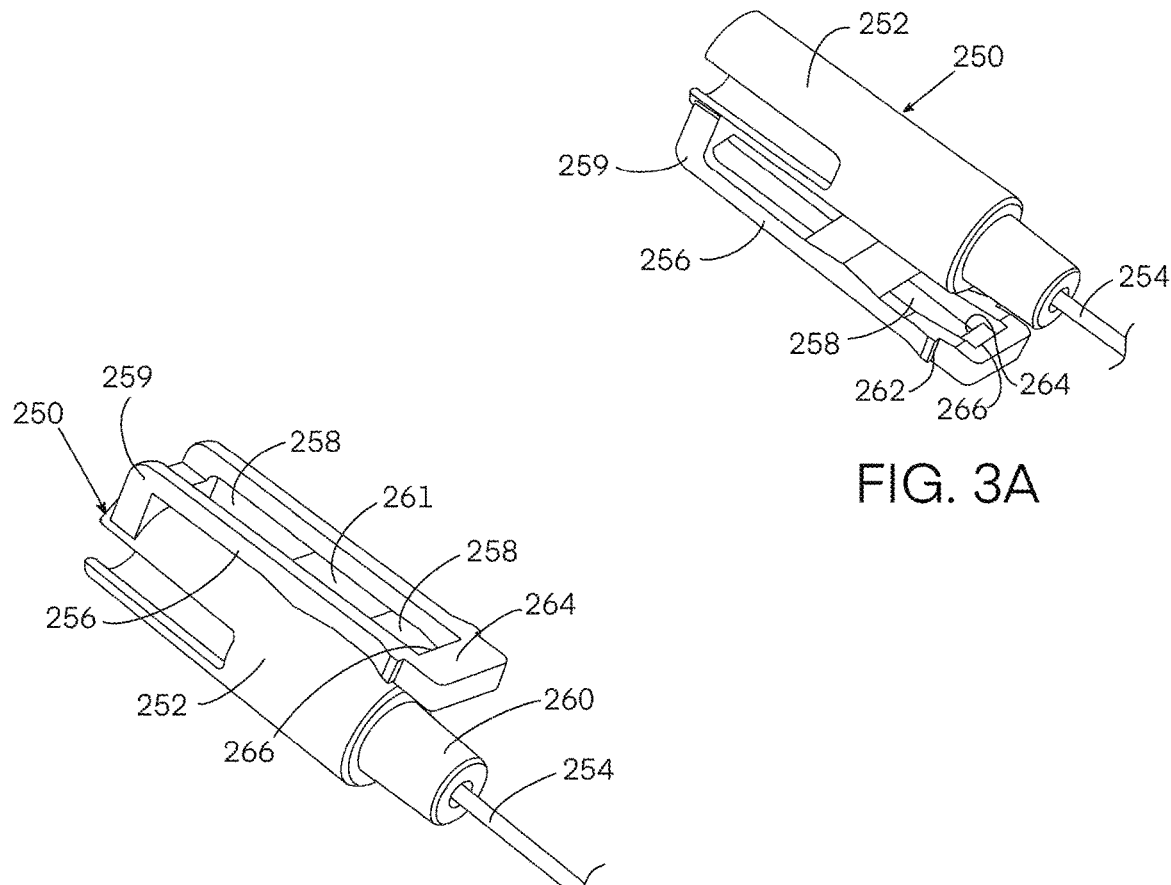
FIG. 3A also shows the support/shield assembly including a locking arm having a plurality of locking surfaces and guide surfaces.
Figure 3B:
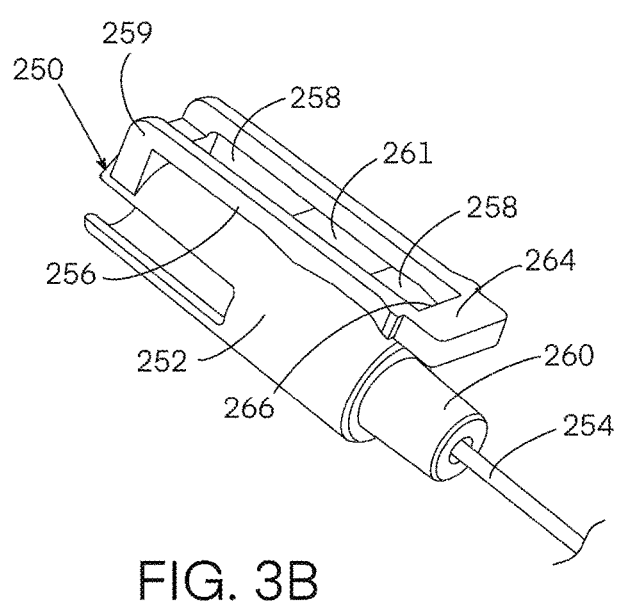
FIG. 3B illustrates a bottom oblique perspective view of the support/shield assembly of FIG. 3A.
Figure 3C:
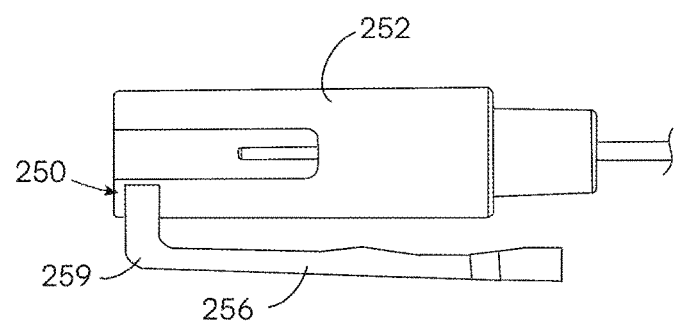
FIG. 3C illustrates the support/shield assembly of FIG. 3A with the locking arm bending at the hinge to assume a natural, unrestrained position away from the support/shield hub.

FIGS. 3A to 3C illustrate a variation of a support/shield assembly 250 for use with the catheter assemblies disclosed herein. FIG. 3A illustrates a top oblique perspective view of a support/shield assembly 250 having a seat 260 that receives a catheter hub (not shown in FIGS. 3A to 3C). The seat 260 can comprise any standard male luer tapered shape or the shape can be any shape that allows seating of the catheter hub. A support/shield 254 extends from the support/shield hub 252 and/or seat 260. The support/shield 254 can comprise any material that both supports a wall of the catheter tubing during insertion of the catheter-needle assembly as well as shields the sharp tip of the cannula upon removal of the needle assembly. For example, the support/shield can comprise any medically approved material used for catheters/sheaths/dilators/etc. In addition, variations of the support/shield can comprise polymers, shape memory alloys, metals and metallic alloys including stainless steel.

FIG. 3A also shows the support/shield assembly 250 including a locking arm 256 having a plurality of locking surfaces 262, 266 and guide surfaces 264. In this variation, the locking arm 256 includes an opening 258 that allows movement of the support/shield assembly 250 within the needle assembly 220 to transition from the ready configuration to the safe configuration disclosed herein. The locking arm 256 of FIG. 3A is shown in a ready configuration, where the locking arm 256 is relatively parallel to the support/shield hub 252. As noted below, the locking arm 256 has a natural position, when unrestrained, to deflect away from the support/shield hub 252. In the variation illustrated in FIG. 3A, the locking arm 256 includes a living hinge 259 that biases the locking arm 256 away from the support/shield hub 252. However, variations of the support/shield assembly 250 can include any number of spring biased constructions to bias the locking arm 256 away from the support/shield hub 252.

FIG. 3B illustrates a bottom oblique perspective view of the support/shield assembly 250 of FIG. 3A. As shown, the locking arm 256 can include a joining surface 261 that provides support for the locking arm and/or FIG. 3C illustrates the support/shield assembly 250 of FIG. 3A with the locking arm 256 at the hinge 259 to assume a natural, unrestrained position away from the support/shield hub 252. In additional variations, the locking arm 256 can bend along a surface of the locking arm 256 rather than just at the hinge 254. As discussed below, alternate variations of the support/shield assembly will have a locking arm where any portion of the locking arm disengages from a locking surface of a catheter hub and engages a locking surface of a needle hub.

Figure 4A:
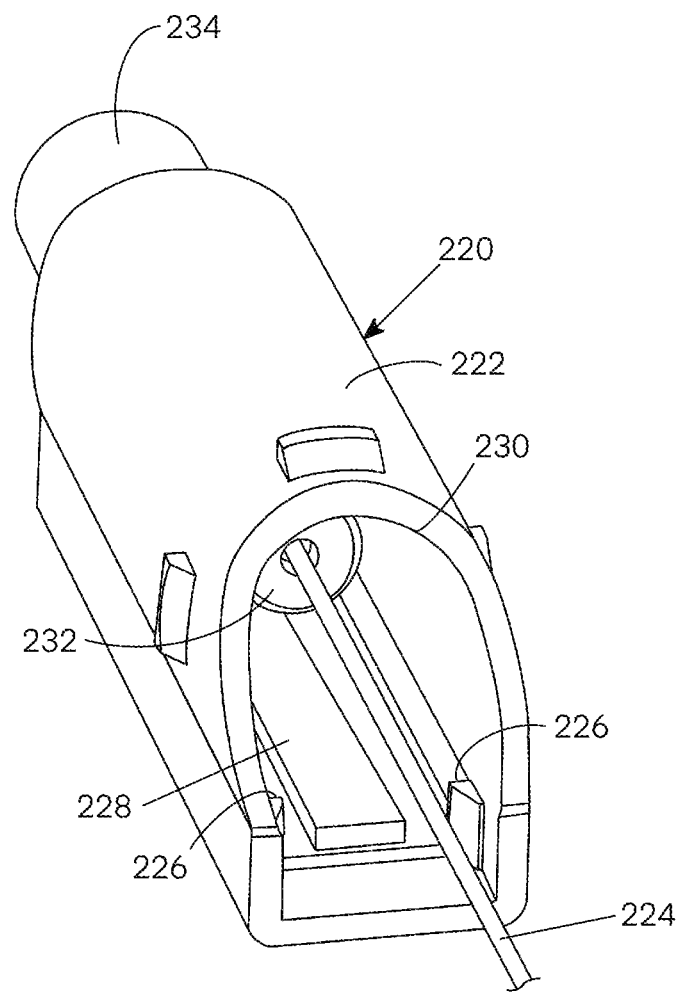
FIG. 4A shows an oblique view of a needle assembly to illustrate the internal chamber of the needle hub.

FIG. 4A shows an oblique view of a needle assembly 220 and illustrates the internal chamber of the needle hub 222. The distal end of the needle hub 222 includes an opening 230 for receiving the support/shield hub 252 and catheter hub 134 (both of which are not shown in FIG. 4A see FIGS. 1A and 2A). The needle hub 222 includes a seat 232 for receiving the support/shield hub 252. The seat can be any structure that receives a hub of the support/shield or catheter. Variations of the needle hub 222 include a male luer. The needle cannula 224 can be coupled through the seat 232 and is secured to the needle hub 222 such that the internal lumen of the cannula 224 can be fluidly coupled to a flash chamber 234. The flash chamber 234 or any part of the needle hub 222 can be transparent to allow a caregiver to observe the presence of blood therein for confirmation that a distal tip of the cannula 224 penetrated a blood vessel. FIG. 4A also shows the needle hub 222 including one or more locking surfaces 226. The needle hub 222 also includes a guide surface 228 that engages a portion of the shield hub. As discussed below, the locking surface 226 and guide surface 228 allow for locking and/or guiding of the components of the needle-catheter assembly between a ready configuration and a locked configuration.

Figure 4B:
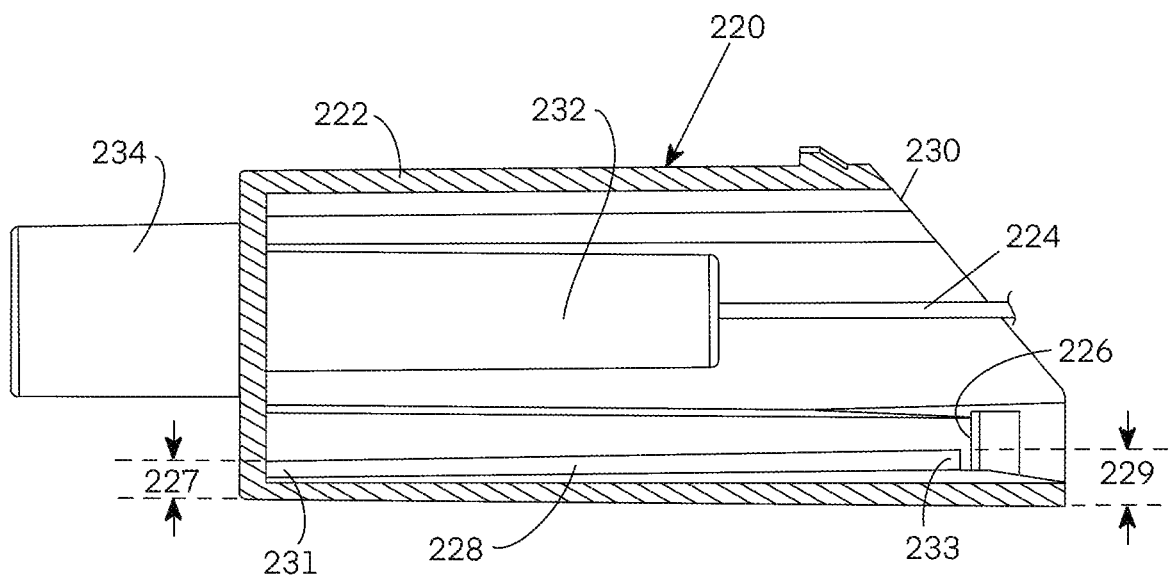
FIG. 4B illustrates a side view of the needle assembly of FIG. 4A with a portion of a wall of the needle hub removed.

FIG. 4B illustrates a side view of the needle assembly 220 with a portion of a wall of the needle hub 222 removed. In the illustrated variation, the guiding surface 228 extends at an incline such that a height 227 of the guide surface 228 at a distal end is greater than a height 227 of the guide surface 228 at the proximal end. Variations of the hub can include inclining the guide surface 228 or inclining the bottom surface of the hub 222. As described below, the incline maintains engagement of the locking arm (256 in FIG. 3A) against a catheter hub until in the ready configuration until the assembly is moved into the safe configuration. FIG. 4B also illustrates the locking surface 226 as being spaced from a distal end of the guide surface 228.

Figure 5A:
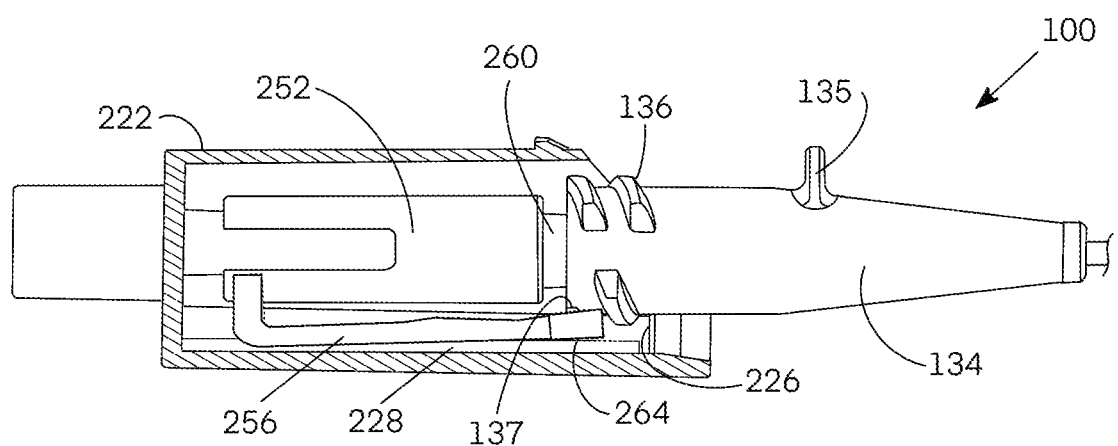
FIG. 5A shows a partial view of a proximal end of a needle-catheter assembly to illustrate a position of the catheter hub and support/shield hub when the needle-catheter assembly is in a ready configuration.
Figure 5B:
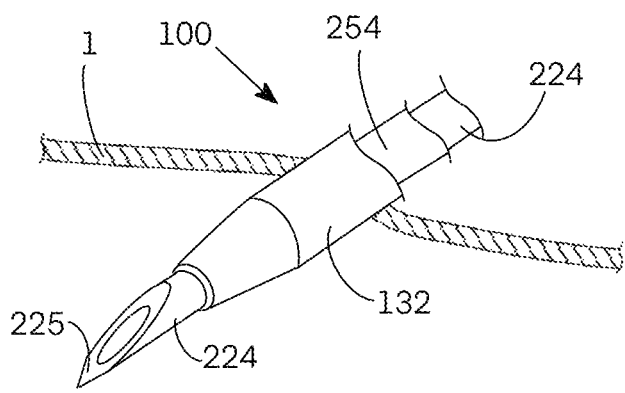
FIGS. 5B and 5C illustrate a state of the distal end of the catheter-needle assembly in the ready configuration when advanced into a vessel.

FIG. 5A shows a partial view of a proximal end of a needle-catheter assembly 100 with a portion of the needle hub 222 removed to illustrate a position of the catheter hub 134 and support/shield hub 252 when the needle-catheter assembly 100 is in a ready configuration. In this particular variation of the needle-catheter assembly 100, the needle hub 222 prevents the caregiver from contacting the support/shield hub 252. Since the assembly 100 is in the ready configuration, the entire assembly 100 can be advanced distally into tissue to insert a tip 225 of the needle 224 into a vessel 1 as shown in FIG. 5B. Once the caregiver confirms placement of the needle 224 into a vessel 1 lumen, the caregiver can actuate the assembly 100, to the safe configuration. As discussed herein, in the ready configuration, the locking arm 256 is maintained/restrained towards the catheter hub 134 and away from its natural position because the guide surface 264 of the locking arm 256 contacts the guide surface 228 of the needle hub 222 (FIG. 5A). By being held against the catheter hub 134 the locking arm 256 engages a surface feature 137 of the catheter hub 134. Accordingly, in this position, the support/shield hub 252 and catheter hub 134 move together as the surface feature 137 of the catheter hub 134 engages a locking surface 266 of the locking arm 256. Therefore, opposite relative movement between the needle hub 222 and the catheter hub 134 causes the support/shield hub 252 to remain engaged with the catheter hub 134. As noted above, alternate variations of the device include the use of the threading 136 of the catheter hub 134 as a locking surface FIG. 5A also shows that a slot 258 (FIGS. 3A and 3B) prevents interference between the locking arm 256 and the guide surface 228 of the needle hub 222 except at the interface between surfaces 228 and 264.

Figure 5C:
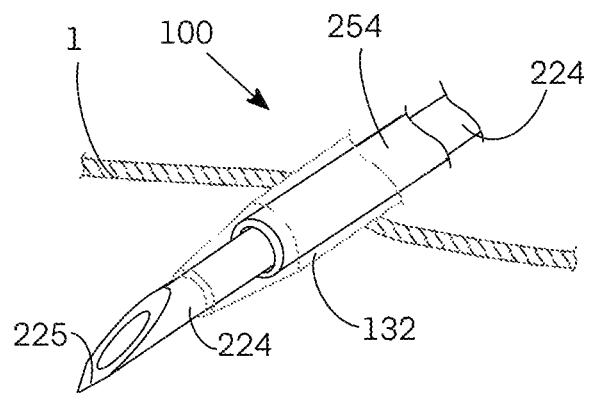

FIGS. 5B and 5C illustrate a state of the distal end of the catheter-needle assembly 100 in the ready configuration when advanced into a vessel 1. The catheter tubing 132, support/shield 254, and needle cannula 224 are partially shown to better illustrate the configuration of these components when the catheter-needle assembly 100 is in the ready configuration. As shown in both FIGS. 5B and 5C, the needle cannula 224 extends through both the support/shield tubing 254 and the catheter tubing 132 but the sharp tip 225 of the cannula 224 extends beyond the support/shield tubing 254, which allows the catheter 132 to end directly onto the cannula 224 adjacent to the tip 225. As noted herein, this configuration allows for 3-4-gauge steps in size difference between the needle cannula 224 and catheter tubing 132. This configuration also permits the support/shield tubing 254 to function as a dilator or reinforcement of the catheter tubing wall 132 given the size differential with the needle cannula 224. FIG. 5C shows the catheter tubing 132 being hidden for purposes of illustrating the end of the support/shield tubing 254, which remains proximal to both the sharp tip 225 and end of the catheter tubing 132.

Figure 6A:
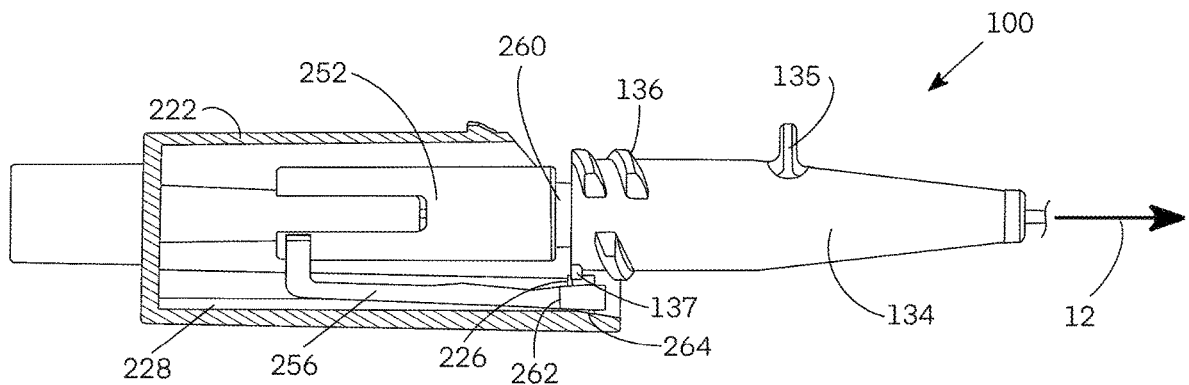
FIG. 6A shows a partial view of a proximal end of a needle-catheter assembly to illustrate a position of the catheter hub and support/shield hub as well as the locking arm when the needle-catheter assembly is moved to the safe configuration.

FIG. 6A shows a partial view of a proximal end of a needle-catheter assembly 100 with a portion of the needle hub 222 removed to illustrate a position of the catheter hub 134 and support/shield hub 252 as well as the locking arm 256 when the needle-catheter assembly 100 is moved to the safe configuration. Typically, the caregiver will observe a flash chamber 234 in the device for confirmation that a lumen of the needle cannula is in fluid contact with a blood vessel. Once the caregiver is comfortable with the placement of the needle-catheter assembly 100, the caregiver manipulates the needle-catheter assembly 100 to produce relative movement between the catheter (typically the catheter hub 134) and the needle hub 222. Typically, the caregiver advances the catheter hub 134 in a distal direction 12 to reduce the possibility of pulling the assembly 100 out of the vessel. However, proximal movement of the needle hub 222 relative to the catheter hub 134 can also suffice. In the illustrated variation, the caregiver can grasp the needle hub 222 and use a finger or thumb to advance the catheter hub 134 using the push-tab or protrusion 135.

Since the catheter-needle assembly 100 was initially in the ready configuration at the start of relative movement between the catheter hub 134 and needle hub 222 (i.e., the configuration shown in FIG. 5A), the support/shield hub 252 is engaged with the catheter hub 134 via interference between locking surfaces on the locking arm 256 and surface feature 137 of the catheter hub 134. Relative movement 12 of the catheter hub 134 to the needle hub 222 also moves the support/shield hub 252 to the condition shown in FIG. 6A where the guide surface 264 of the locking arm 256 is no longer engages the guide surface 228 of the needle hub 222. The resiliency of the locking arm 256 causes locking arm 256 and surface 264 to move moves towards an unrestrained position (e.g., the surface 264 engages the wall of the needle hub 222). Doing so causes disengagement between the locking arm 256 and catheter 134 hub and engagement between a locking surface 262 of the locking arm 256 and locking surfaces (e.g., 226) of the needle hub 222. In this configuration, the locking arm 256 is completely disengaged from the guide surface 228, which prevents the support/shield hub 252 from moving proximally and uncovering of the needle tip 225 (not shown in FIG. 6A). It is noted that the support/shield hub 252 can still be engaged with the needle hub 222. However, the catheter hub 134 and support/shield hub are no longer locked together.

Further distal advancement 12 of the catheter hub 134 causes further separation between the catheter hub 134 and support/shield hub 252 until the catheter hub 134 disengages the seat 260 of the support/shield hub 252. At this stage (as shown in FIG. 6A), the locking arm 256 now locks together the needle hub 222 and support/shield hub 252. Accordingly, withdrawal of the needle hub 222 also causes withdrawal of the support/shield hub 252.

Figure 6B:
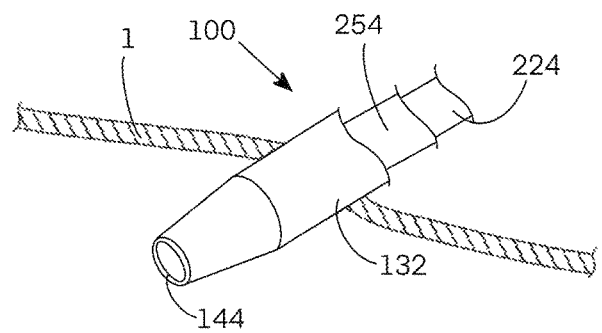
FIGS. 6B and 6C illustrate a state of the distal end of the catheter-needle assembly after the catheter assembly of FIG. 6A moves from the ready configuration to the safe configuration.
Figure 6C:
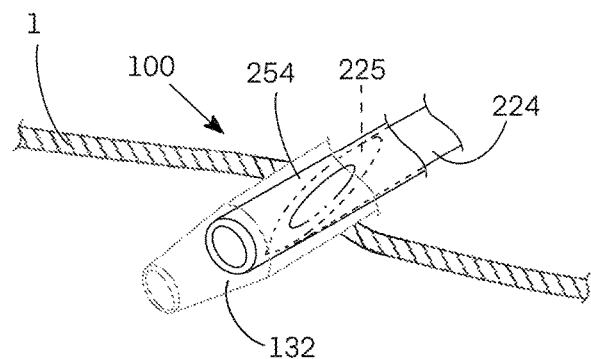

FIGS. 6B and 6C illustrate a state of the distal end of the catheter-needle assembly 100 after the catheter assembly moves from the ready configuration (FIG. 5A) to the safe configuration (FIG. 6A). As shown in FIG. 6B, the distal opening 144 of the catheter 132 are within the vessel 1. However, the sharp tip 225 of the cannula 224 is withdrawn relative to the catheter tubing 132. FIG. 6C illustrates the state of the distal end of the catheter assembly with the catheter tubing 132 in phantom view to better illustrate the positioning of the sharp tip 225 relative to the support/shield tubing 254. Movement of the catheter hub relative to the needle hub from the ready configuration to the safe configuration will occur over a distance that allows the catheter tube 132 and support/shield tube 245 to a position that is distal to the sharp tip 225. Again, as shown in FIG. 5A, which shows the ready configuration, the catheter hub and support/shield hub are locked together. Movement of the catheter hub from this position also moves the support/shield hub until both enter the safe configuration of FIG. 6A. The distance of the movement will be enough to position the catheter hub 132 and support/shield tube 254 distal to the sharp tip 225 and cannula 224 as shown in FIG. 6C.

Figure 7A:
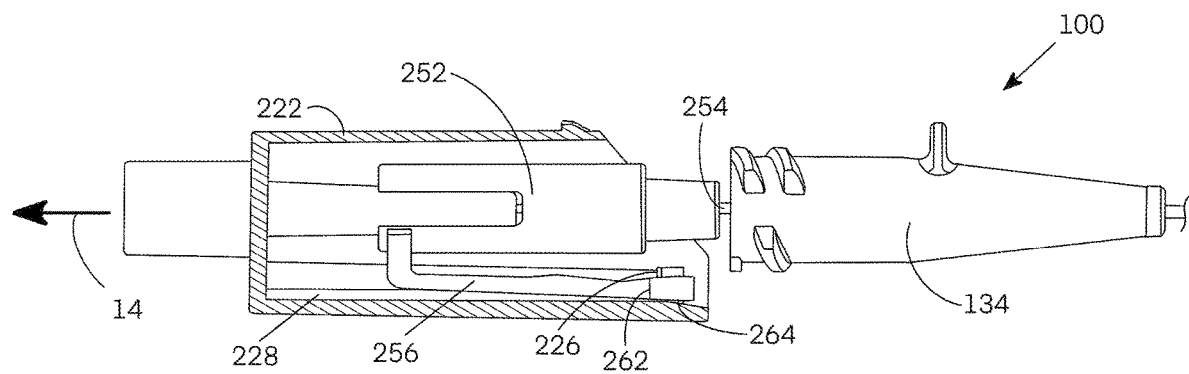
FIG. 7A illustrates the state of the catheter-needle assembly in the safe configuration as the needle hub retracts from the catheter hub.

FIG. 7A illustrates the state of the catheter-needle assembly 100 in the safe configuration as the needle hub 222 retracts from the catheter hub 134. As discussed above, the needle hub 222 is locked with the support/shield hub 252 by interference between locking surfaces 262 of the locking arm 256 and one or more locking surfaces 226 of the needle hub 222. Withdrawal of the needle hub 222 in a proximal direction 14 relative to the catheter hub 134 causes the withdrawal of both the needle hub 222 and the support/shield hub 252 such that the needle cannula remains secured within the support/shield tubing 254 such that the blunted tip of the support/shield tubing protects the caregiver or others from skin penetration by the sharp tip of the cannula.

Figure 7B:
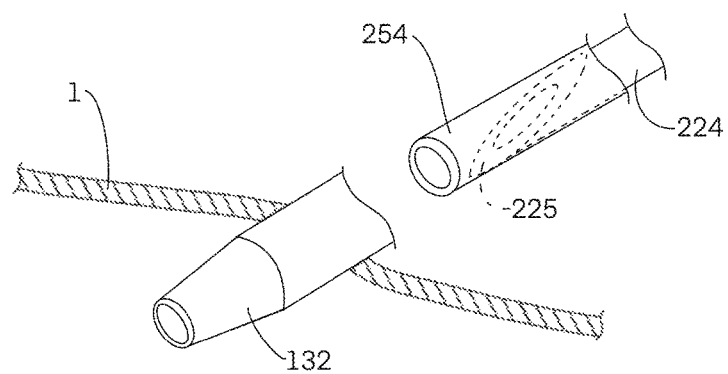
FIG. 7B illustrates a state of the distal end of the catheter needle assembly of FIG. 7A, where the needle cannula is locked together with the support/shield tubing.

FIG. 7B illustrates a state of the distal end of the catheter needle assembly 100 of FIG. 7A, where the needle cannula 224 is locked together with the support/shield tubing 254 thorough locking of their respective hubs. As shown, the sharp tip 225 of the needle cannula 224 remains secured within the support/shield tubing 254. Ultimately, the support/shield tubing 254 and needle cannula 224 are removed from the catheter tubing 132, which remains in the vessel 1.

Figure 7C:
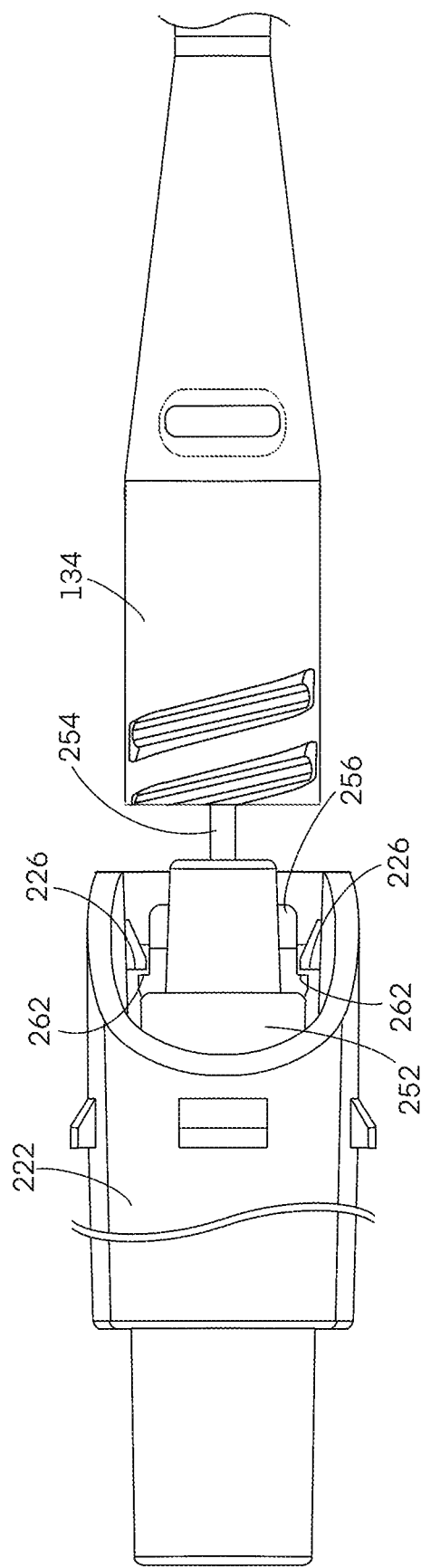
FIG. 7C shows a top view of the support/shield hub located within the needle hub when in the safe configuration.

FIG. 7C shows a top view of the support/shield hub 252 located within the needle hub 222 when in the safe configuration. As shown, dropping of the locking arm 256 from the guide surface (not visible in FIG. 7C) of the needle hub 222 causes locking surfaces 262 of the locking arm to engage locking surfaces 226 of the needle hub 222. Any number of locking surfaces can be used in alternate variations of the device. Once secured in the safe configuration, the needle and support/shield assemblies can be removed from the catheter.

Figure 8A:
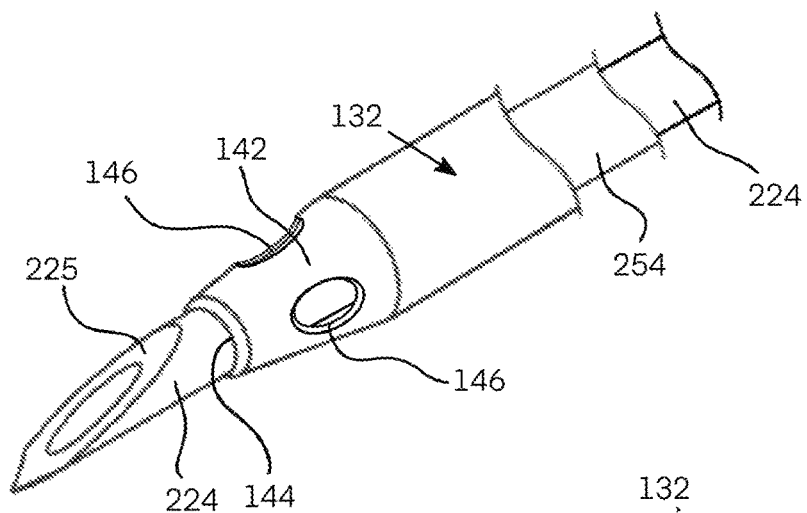
FIG. 8A shows a magnified partial view a distal end of a catheter assembly similar to that shown in FIG. 1A.

FIG. 8A shows a magnified partial view a distal end of a catheter assembly similar to that shown in FIG. 1A. As shown in FIG. 8A, a support/shield member 254 is positioned between the needle cannula 224 and catheter tubing 132.

Figure 8B:
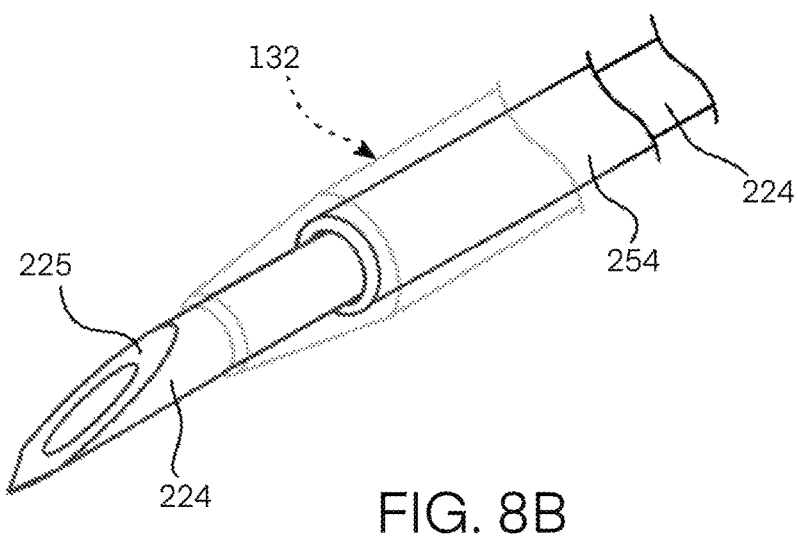
FIGS. 8B and 8C illustrate additional possible variations of distal end of needle assemblies.
Figure 8C:
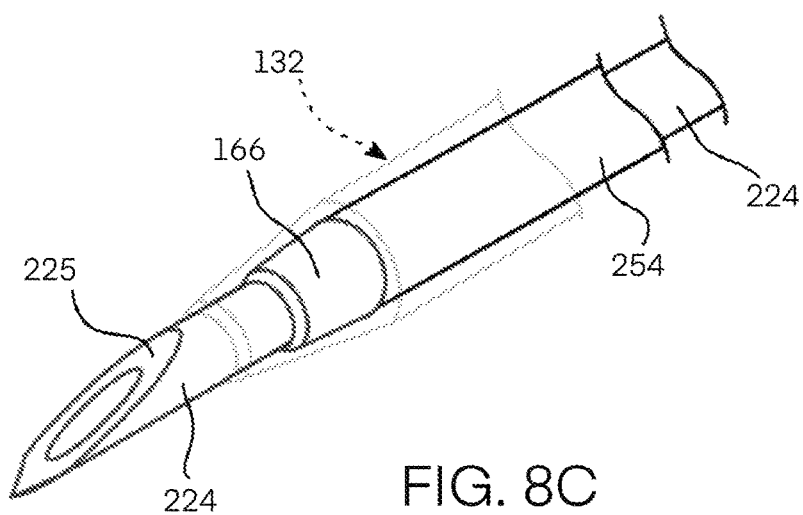

FIGS. 8B and 8C illustrate additional possible variations of distal end of needle assemblies. In FIGS. 8B and 8C the catheter tubing 132 is faded/phantom view to better illustrate the support/shield member 254 located between the needle 224 and catheter tubing 132. As shown, the support/shield member 254 extends along the needle 224 but terminates within the catheter tubing 132. The distal end of the of the support/shield member 254 can be blunted as shown in FIG. 8B or can be tapered 166. In the illustrated variation, the tapered portion 255 of the support/shield member 254 is located within a taper of the catheter tubing 132. However, alternate variations are within the scope of this disclosure. For example, the support/shield member 254 can be stepped or have any configuration as used by those skilled in the art.

FIG. 8A also illustrates optional flow openings 146 extending through a wall of the catheter tubing 132. Such flow openings 146 can assist in offsetting any restriction of flow through the catheter 132 due to the reduced size of the distal opening 144 relative to a lumen size of the catheter tubing 132.

Figure 9A:
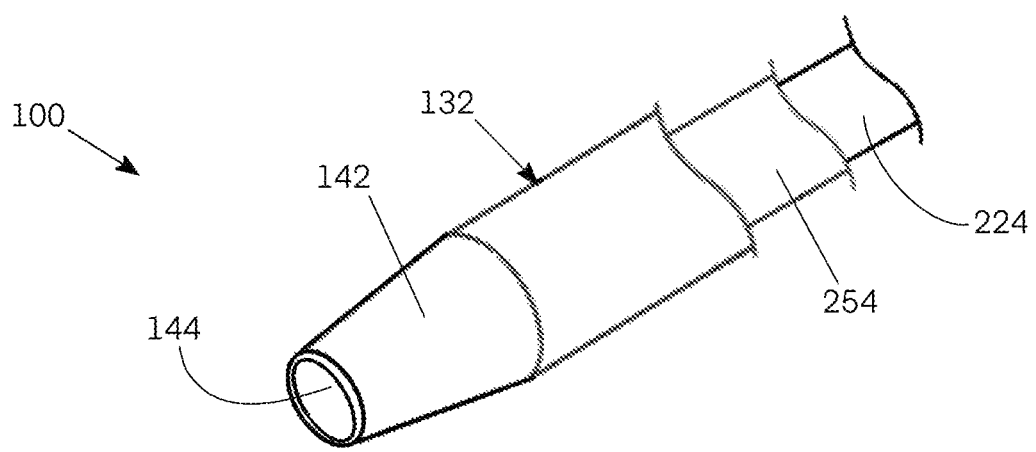
FIG. 9A shows a partial view of the distal end of the needle assembly of FIG. 8A where the needle cannula is withdrawn relative to the catheter tubing and support/shield member.
Figure 9B:
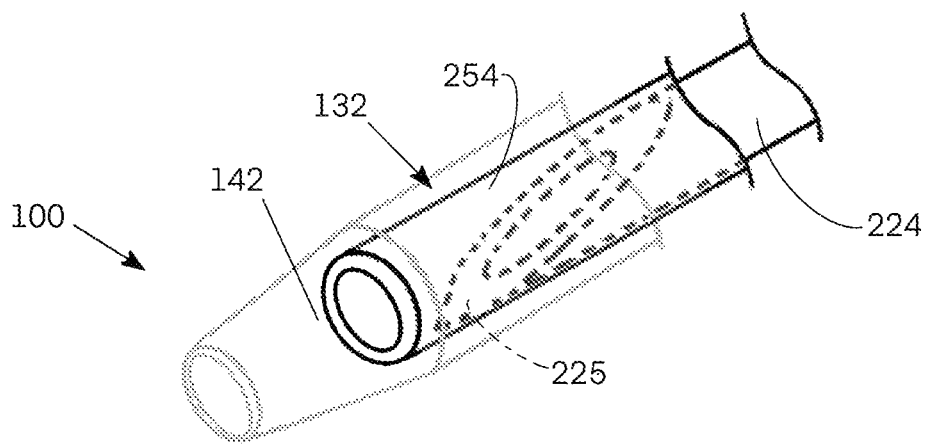
FIGS. 9B and 9C show catheter tubing as faded/hidden to better illustrate the location of the needle relative to the support/shield member and catheter tubing.
Figure 9C:
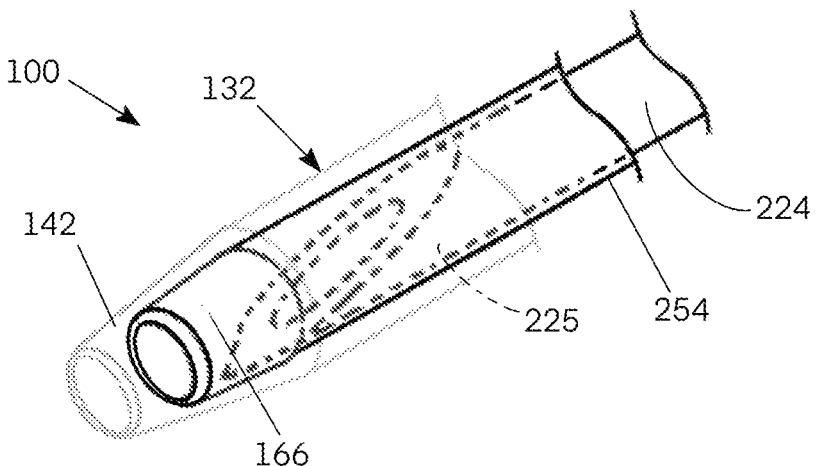

FIG. 9A shows a partial view of the distal end of the needle assembly 100 of FIG. 8A where the needle cannula 224 is withdrawn relative to the catheter tubing 132 and support/shield member 254. In FIGS. 9B and 9C the catheter tubing 132 is shown as faded/hidden to better illustrate the location of the needle 224 relative to the support/shield member 254 and catheter tubing 132. As shown, the bevel 178 or sharp tip of the needle 224 is retracted within the support/shield member 254 to shield the sharp tip upon removal of the needle 224 from the catheter 132 as discussed above. FIG. 9C illustrates another variation of the assembly 100 where the support/shield member 254 includes a tapered distal portion 166 within a tapered distal end 142 of the catheter 132. As shown, a bevel 178 is retracted within the support/shield member 224 to shield the sharp tip of the needle 224.

Figure 10A:
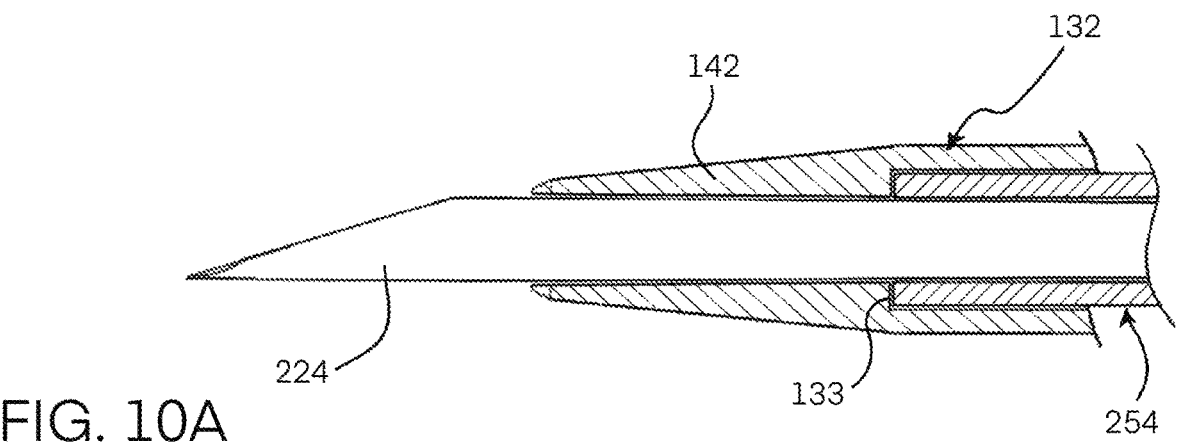
FIGS. 10A and 10B illustrate partial cross-sectional views of the catheter and support/shield member of FIGS. 9B and 9C respectively.
Figure 10B:
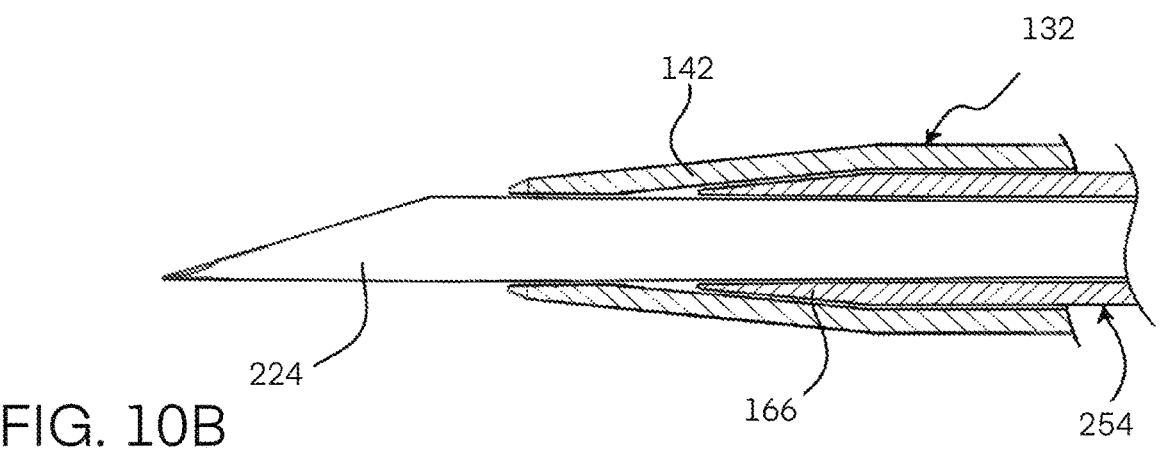

FIGS. 10A and 10B illustrate partial cross-sectional views of the catheter 132 and support/shield member 254 of FIGS. 9B and 9C respectively. FIG. 10A illustrates the needle 170 extending through the support/shield member 254 and out through the catheter 132. The support/shield member 254 is slidable or retractable relative to the catheter 132 but is prevented from moving distally in the catheter 132 due to the presence of a shoulder 133 within the catheter 132. The shoulder 133 is formed from an increase in a thickness of the catheter wall at the tapered section 142. This increased wall thickness reduces the risk of collapse at the tapered section 142 when inserted into tissue. FIG. 10B illustrates a variation where the support/shield member 254 includes a tapered section 166 that is positioned within the tapered section 142 of the catheter 132. In the illustrated variation, the taper 166 of the support/shield member 254 can support the catheter 132 at the tapered section 142 of the catheter 132 when inserted within tissue.

Another benefit of the variations shown in FIGS. 8A to 10B is that the intermediate member not only provides a needle guard when the needle is retracted within the intermediate member, but the intermediate member also reinforces the catheter, which allows for a greater size differential between the catheter and needle. This allows for the placement of a smaller gauge needle to insert a given catheter.

The configurations disclosed herein not only allow for an improved safety mechanism, but the configuration of needle cannula, support/shield tubing, and catheter allow improved sizing between the smaller needle and larger catheter than are otherwise available. Hypodermic needles are available in a wide variety of outer diameters described by gauge numbers. Smaller gauge numbers indicate larger outer diameters. Inner diameter depends on both gauge and wall thickness. Needles are routinely available in a variety of gauge sizes, including 18, 21, 23, and 25 gauge.

For example, conventional needle catheter assemblies, especially for peripheral catheters, are configured so that any given catheter size uses a needle size that is two gauge sizes removed from the catheter gauge (for purposes of discussion the outer diameter size of the catheter and needle are measured by gauge size but other measurements are within the scope of this disclosure). FIG. 11A shows two tables, the first being a conventional needle and catheter size comparison based on ISO standards for needle that are 2-gauge sizes smaller than their associated catheter. As shown, the configuration column indicates catheter size with the associated needle size being 2-gauge sizes smaller. The lower chart illustrates examples of various conventional needle catheter devices from various medical device manufacturers. Like the ISO standards, a measurement of the commercially available needle catheter assemblies confirms a 2-gauge size differential between the catheter and needle.

In contrast, FIG. 11B illustrates various configurations of catheter needle assemblies constructed in accordance with the present disclosure. As shown, the construction of the catheter needle assemblies described herein allow for a 4-gauge size differential between the catheter and needle. The catheter assemblies of the present disclosure can also allow for a 3-gauge size differential as well.

The needle gauge becomes a consideration in certain cases where the vein of the patient is narrow, fragile, or superficial. In such cases, a gauge size with a larger number (e.g., 25 G) may be preferred over a routine needle gauge (e.g., 21 G) to minimize damage to the blood vessel, as well as minimize the associated pain during insertion.

However, while a larger gauge size needle has a smaller outer diameter, the needle also has a smaller bore and a smaller internal diameter. When blood cells are forced by the vacuum pressure of large volume evacuated and quickly enters the tight space of a tiny needle gauge, hemolysis may occur. Hemolysis can cause inaccurate results (slight to significant) when testing several analytes. Potassium, for example, can be falsely increased in a hemolyzed sample. Phlebotomists must exercise judgment between maintaining patient comfort and maximizing sample integrity when selecting an appropriate needle gauge for each patient.

The previous description of the disclosed embodiments is provided to enable any person skilled in the art to make or use the present invention. Various modifications to these embodiments will be readily apparent to those skilled in the art, and the generic principles defined herein can be applied to other embodiments without departing from the spirit or scope of the invention. For example, a wide variety of materials may be chosen for the various components of the embodiments. It is therefore desired that the present embodiments be considered in all respects as illustrative and not restrictive, reference being made to the appended claims as well as the foregoing descriptions to indicate the scope of the invention.

The invention claimed is:

1. A medical assembly for insertion into tissue, the medical assembly comprising:
a cannula assembly comprising a cannula hub and a cannula member extending to a cannula distal end;
a shield assembly comprising a shield hub and a shield member extending to a shield distal end, where the shield hub is configured to be received in the cannula hub and the shield member is configured to concentrically receive the cannula member, where the shield assembly is configured to move from a ready configuration to a safe configuration;
a tubing assembly comprising a tubing hub and a tubing extending to a tubing distal end, where the tubing assembly is configured to be received in the cannula hub over the shield hub and where the tubing is configured to concentrically receive the shield member;
wherein in the ready configuration the shield hub is releasably locked to the tubing hub, the cannula distal end extends beyond both the shield distal end and the tubing distal end to permit insertion into tissue, and the shield distal end remains within the tubing;
where, when in the ready configuration, relative movement between the tubing hub and the cannula hub by a first distance causes movement of the shield assembly to the safe configuration; and
wherein in the safe configuration, the shield hub is released from the tubing hub and mechanically interferes with the cannula hub to become locked thereto, and the shield distal end now extends distally to the cannula distal end while remaining within the tubing.

2. The medical assembly of claim 1, wherein the cannula distal end comprises a sharp tip.

3. The medical assembly of claim 1, wherein the shield hub further comprises a locking arm that is spring biased away from the shield hub and the cannula hub comprises a first guide surface within an interior of the cannula hub, wherein in the ready configuration the locking arm is urged against the tubing hub by the first guide surface to releasably lock the shield hub to the tubing hub.

4. The medical assembly of claim 3, wherein the interior of the cannula hub further includes a first locking surface spaced from the first guide surface and wherein in the safe configuration, the locking arm disengages from the first guide surface causing the locking arm to bias away from the tubing hub towards the cannula hub such that a second locking surface of the locking arm mechanically interferes with the first locking surface to prevent distal movement of the shield hub out of to the cannula hub.

5. The medical assembly of claim 4, wherein in the safe configuration the locking arm entirely disengages from the first guide surface.

6. The medical assembly of claim 4, wherein in the safe configuration the locking arm mechanically interferes with the first guide surface to prevent proximal movement of the shield hub within the cannula hub.

7. The medical assembly of claim 1, wherein the shield member reinforces the tubing to permit the tubing to have a gauge difference of at least 3 sizes between the tubing and the cannula member.

8. The medical assembly of claim 1, wherein the tubing distal end comprises a plurality of openings.

9. The medical assembly of claim 1, wherein the tubing comprises a catheter tubing and the cannula member comprises a needle.

10. The medical assembly of claim 1, wherein the shield distal end comprises a blunted distal end.

11. The medical assembly of claim 1, wherein a portion of the cannula hub comprises a flash chamber configured to visually confirm fluids in the cannula hub.

12. A medical assembly for insertion into tissue, the medical assembly comprising:
a cannula assembly having a cannula hub and a cannula having a cannula distal end, the cannula hub having an interior chamber with a first guide surface and a first locking surface;
a shield assembly comprising a shield hub and a shield member having a shield distal end, the shield hub configured to be received within the interior chamber of the cannula hub such that the cannula is coaxially received in the shield member, the shield hub comprising a locking arm having a second locking surface and a second guide surface, the locking arm also having an intermediate portion extending between a fixed portion and a free portion, where the fixed portion is coupled to the shield hub and the free portion is spring-biased away from the shield hub, the shield assembly being moveable between a ready configuration and a safe configuration;
a tubing assembly comprising a tubing hub and a tubing member having a tubing distal end, wherein the tubing hub is configured for positioning on the shield hub and the tubing member coaxially receives the shield member, the tubing hub comprising a surface feature;
wherein in the ready configuration the cannula distal end extends distally beyond both the shield distal end and the tubing distal end and where the first guide surface engages the second guide surface to constrain the free portion of the locking arm against the surface feature of the tubing hub to releasably lock the shield hub to the tubing hub;
wherein, when in the ready configuration, axial separation of the tubing hub from the cannula hub over a first distance causes the shield assembly to assume the safe configuration where the second guide surface disengages from the first guide surface causing the free portion to bias away from and disengage the tubing hub, and where the shield distal end is now positioned distal to the cannula distal end, and where interference between the second locking surface against the first locking surface prevents further axial separation of the shield hub from the cannula hub to permit separation of the tubing assembly from the shield assembly and the cannula assembly.

13. The medical assembly of claim 12, wherein the cannula distal end comprises a sharp tip.

14. The medical assembly of claim 12, wherein the shield member reinforces the tubing member to permit the tubing member to have a gauge difference of at least 3 sizes between the tubing member and the cannula.

15. The medical assembly of claim 12, wherein the tubing distal end comprises a plurality of openings.

16. The medical assembly of claim 12, wherein the tubing member comprises a catheter tubing and the cannula comprises a needle.

17. The medical assembly of claim 12, wherein the shield distal end comprises a blunted distal end.

18. The medical assembly of claim 12, wherein a portion of the cannula hub comprises a flash chamber configured to visually confirm fluids in the cannula hub.

19. A method of inserting a medical assembly into tissue and removing the medical assembly from tissue in a safe condition, the method comprising:
positioning the medical assembly adjacent to tissue where a cannula end of a cannula extends distally from a tubing end of a tubing and where a shield member is located between the cannula and the tubing, the shield member having a shield end that is located within the tubing, and where medical assembly includes a cannula hub joined to the cannula, a tubing hub joined to the tubing, and a shield hub joined to the shield member, where the tubing hub is seated on the shield hub and releasably locked thereto, and the shield hub is seated on the cannula hub;
inserting the cannula end and the tubing end into tissue to a desired location;
moving the tubing hub relative to the cannula hub such that the shield hub moves with the tubing hub causing the shield end to be positioned distally to the tubing end while remaining within the tubing, and causing the shield hub to release from the tubing hub while mechanically locking with the cannula hub; and
removing the shield member and the cannula from the tubing and the tubing hub such that the shield member covers the cannula to establish the safe condition.

20. The method of claim 19, further comprising visually identifying a fluid within the cannula hub prior to removing the shield member and the cannula from the tubing.

21. A medical assembly comprising:
a cannula extending from a cannula hub to a cannula distal end;
a shield member extending from a shield hub to a shield distal end, the shield member positioned over the cannula, where the shield distal end is located proximally to the cannula distal end;
a tubing extending from a tubing hub to a tubing distal end, the tubing positioned over the shield member, where the tubing distal end extends distally to the shield distal end such that the tubing distal end tapers to contact the cannula at a location distally to the shield member;
wherein the cannula includes a protected position when the cannula is moved proximal relative to both the shield member and tubing such that the cannula distal end is located within the shield member; and
wherein separation of the shield hub and the tubing hub causes locking of the cannula hub and the shield hub to permit removal of the shield member and the cannula from the tubing.

22. The medical assembly of claim 21, wherein the shield member reinforces the tubing to permit the tubing to have a gauge difference of at least 3 sizes between the tubing and the cannula.

\* \* \* \* \*